(12) United States Patent
Chen et al.

(10) Patent No.: US 12,274,783 B2
(45) Date of Patent: Apr. 15, 2025

(54) MICROBUBBLE DISPERSION SYSTEM STABILIZED WITH POLYDOPAMINE NANOPARTICLES FOR HIGHLY-EFFICIENT INTRAVENOUS OXYGEN SUPPLY AND METHOD FOR PREPARING THE SAME

(71) Applicant: ZHEJIANG UNIVERSITY, Hangzhou (CN)

(72) Inventors: Dong Chen, Hangzhou (CN); Zhu Sun, Hangzhou (CN); Boheng Wu, Hangzhou (CN); Jianpeng Sheng, Hangzhou (CN); Tingbo Liang, Hangzhou (CN); Xiaowei Zhai, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 854 days.

(21) Appl. No.: 17/502,010

(22) Filed: Oct. 14, 2021

(65) Prior Publication Data

US 2022/0105034 A1  Apr. 7, 2022

Related U.S. Application Data

(63) Continuation of application No. PCT/CN2020/128750, filed on Nov. 13, 2020.

(30) Foreign Application Priority Data

Dec. 30, 2019 (CN) .......................... 201911400445.8

(51) Int. Cl.
| | |
|---|---|
| *A61K 9/10* | (2006.01) |
| *A61K 9/00* | (2006.01) |
| *A61K 33/00* | (2006.01) |
| *A61K 47/34* | (2017.01) |
| *B82Y 5/00* | (2011.01) |
| *B82Y 40/00* | (2011.01) |

(52) U.S. Cl.
CPC .............. *A61K 9/10* (2013.01); *A61K 9/0026* (2013.01); *A61K 33/00* (2013.01); *A61K 47/34* (2013.01); *B82Y 5/00* (2013.01); *B82Y 40/00* (2013.01)

(58) Field of Classification Search
None
See application file for complete search history.

(56) References Cited

FOREIGN PATENT DOCUMENTS

| CN | 107537044 A | | 1/2018 | |
|---|---|---|---|---|
| CN | 109453398 A | * | 3/2019 | ......... A61K 41/0052 |
| CN | 111067872 A | | 4/2020 | |
| WO | 2016083533 A1 | | 6/2016 | |

OTHER PUBLICATIONS

Wang (Influence of polydopamine-mediated surface modification on oxygen-release capacity of haemoglobinbased oxygen carriers, Mar. 26, 2018, Artificial Cells, Nanomedicine, and Biotechnology, vol. 26, No. 53, S484-S492) (Year: 2018).*
Cavalli (Preparation and in vitro characterization of chitosan nanobubbles as theranostic agents, Mar. 14, 2015, Colloids and Surfaces B: Biointerfaces, 129:39-46) (Year: 2015).*
Yang (Polydopamine gradients by oxygen diffusion controlled autoxidation, 2013, Chem. Commun, 49:10522-10524) (Year: 2013).*
International Search Report (PCT/CN2020/128750); Date of Mailing: Feb. 18, 2021.
"Influence of polydopamine-mediated surface modification on oxygen-release capacity of haemoglobin-based oxygen carriers" (May 10, 2018) [Quan Wang et al.].
"Preparation and Characterization of Chitosan Nanobubbles" (Mar. 31, 2019) [Xuemei Gao et al.].

* cited by examiner

*Primary Examiner* — Michael G. Hartley
*Assistant Examiner* — Kaila A Craig
(74) *Attorney, Agent, or Firm* — Wiersch Law Group

(57) ABSTRACT

The present application discloses a microbubble dispersion system stabilized with polydopamine nanoparticles for highly-efficient intravenous oxygen supply and a method for preparing the same. The method includes: dissolving dopamine, chitosan quaternary ammonium salt and amino-rich polymer in water, adjusting the pH to be alkaline, and then introducing oxygen into the solution; under the strong shear force of a homogenizer, oxygen oxidizing dopamine, and the obtained polydopamine nanoparticles adhering to the interface of oxygen microbubbles during polymerization, forming a compact shell layer of polydopamine particles; finally, adding glutaraldehyde to solidify the shell layer of polydopamine particles adhered to the interface of microbubbles, and obtaining oxygen microbubbles stably dispersed in water by filtration, washing and redispersion. The oxygen microbubbles stabilized with polydopamine nanoparticles have excellent biocompatibility, can realize rapid and efficient delivery of oxygen, and thus have an important application value in the field of highly-efficient intravenous oxygen supply.

5 Claims, 5 Drawing Sheets

MICROBUBBLE DISPERSION SYSTEM STABILIZED WITH POLYDOPAMINE NANOPARTICLES FOR HIGHLY-EFFICIENT INTRAVENOUS OXYGEN SUPPLY AND METHOD FOR PREPARING THE SAME

TECHNICAL FIELD

The present application relates to the field of nanotechnology, in particular to a microbubble dispersion system stabilized polydopamine nanoparticles for intravenous efficient oxygen supply and a method for preparing the same.

BACKGROUND

Intravenous oxygen supply has always been an important challenge for people. Asphyxiating cardiac arrest often occurs in patients with severe or long-term hypoxia. When the oxygen in blood is too low, the heart stops beating and oxygen stops being delivered to living organs. If the blood oxygen level cannot be recovered quickly, it will lead to organ damage and death within a few minutes. At present, patients with asphyxiating cardiac arrest are mainly rescued by oxygen inhalation, intubation or mechanical ventilation. However, when these treatments cannot improve the oxygen content in patients' blood quickly, they may directly threaten the life and health of patients, resulting in higher mortality rate of the disease.

Intravenous oxygen supply is an effective method to rapidly increase the oxygen content in blood, which can make patients get out of danger quickly. However, due to the low solubility of oxygen in blood, oxygen cannot be directly injected into vein. Researchers prepared a microbubble dispersion liquid by shearing an aqueous solution containing surfactant molecules at a high speed, and then injected the microbubble dispersion liquid into blood by intravenous injection in vitro, so as to achieve the effect of rapid oxygen supply. However, the microbubble dispersion system stabilized with surfactant molecules is unstable and prone to coalescence of microbubbles. Under the Ostwald Ripening effect, the gas will gradually transfer from smaller microbubbles to larger microbubbles, eventually leading to larger and larger diameters of the microbubbles. Therefore, it is still an urgent problem to prepare a biocompatible, stable and dispersed microbubble system and realize efficient intravenous oxygen supply.

According to the present application, biocompatible dopamine is adopted as a material, and a microbubble dispersion system stabilized with polydopamine nanoparticles for highly-efficient intravenous oxygen supply is prepared. The microbubble dispersion system has good dispersibility and stability in water, can realize rapid and efficient delivery of oxygen, and thus has an important application value in the field of highly-efficient intravenous oxygen supply.

SUMMARY

Aiming at the defects of the prior art, the present application discloses a microbubble dispersion system stabilized with polydopamine nanoparticles for highly-efficient intravenous oxygen supply and a method for preparing the same. In the method, dopamine is oxidized by oxygen, and polydopamine nanoparticles are adhered to the interface of oxygen microbubbles during polymerization to form a compact shell layer of polydopamine particles. The prepared oxygen microbubble system stabilized with polydopamine nanoparticles has excellent biocompatibility, can realize rapid and efficient delivery of oxygen, and thus has an important application value in the field of intravenous efficient oxygen supply.

To achieve the above purpose, the present application provides the following solution.

A method for preparing a microbubble dispersion system stabilized with polydopamine nanoparticles for highly-efficient intravenous oxygen supply according to the present application includes the following steps:

(1) dissolving dopamine, a chitosan quaternary ammonium salt and polylysine in deionized water, and then adding a tris buffer solution to adjust a pH value of a mixed solution to make the mixed solution alkaline;

(2) introducing oxygen into the solution obtained in the step (1), shearing the oxygen into microbubbles by using a high-speed dispersion homogenizer, oxidizing and self-polymerizing the dopamine under alkaline conditions to form polydopamine nanoparticles, which adhere to an interface of the microbubbles to form a compact shell layer of polydopamine particles, then turning off the high-speed dispersion homogenizer, and continuously introducing oxygen until the solution is brownish black;

(3) adding a glutaraldehyde solution into the solution obtained in the step (2), fully mixing with the high-speed dispersion homogenizer, and then stirring to solidify the shell layer of polydopamine particles adhered to the interface of the microbubbles;

(4) diluting a stable microbubble dispersion solution of the polydopamine nanoparticles obtain in the step (3), filtering and washing to remove redundant polydopamine nanoparticles and reagents which are not adsorbed on the interface of the microbubbles, and finally obtaining a stable oxygen microbubble dispersion system with the polydopamine nanoparticles stably dispersed in water.

Preferably, in step (1), a concentration of the dopamine is 10-40 mg/mL, a concentration of the polylysine is 1-40 mg/ml, and a concentration of the chitosan quaternary ammonium salt is 20-400 mg/ml; a mass ratio of the polylysine to the dopamine is 0.25-1; a mass ratio of the chitosan quaternary ammonium salt to the dopamine is 2-10.

Preferably, the adding a tris buffer solution to adjust a pH value of a mixed solution to make the mixed solution alkaline is adding Tris-HCl to the mixed solution to adjust the pH value of the mixed solution to 7.5-9.0.

Preferably, in the step (2), a flow rate of introducing oxygen is 0.5-2 L/min, the rotating speed of the high-speed dispersion homogenizer is 10,000 rpm-14,000 rpm, and the homogenization time is 3-6 min; introduction of oxygen is continued for 1-5 min until the solution is brownish black.

Preferably, in the step (3), a volume fraction of the glutaraldehyde solution is 2%-6.5%, and a dosage of the glutaraldehyde solution is 1 ml-5 ml; a rotating speed of the high-speed dispersion homogenizer is 10000 rpm-14000 rpm, and a homogenization time is 1-4 min; the stirring is carried out at 20-40° C. for 30 min to 2 h;

Preferably, in the step (4), a pore diameter of a filter paper is 1 μm-11 μm.

The present application further discloses an oxygen microbubble dispersion system stabilized with polydopamine particles prepared by the method. The system has excellent biocompatibility, can stably carry oxygen for a long time, and can quickly and efficiently release oxygen in an extremely anoxic solution to provide oxygen for anoxic tissues, and thus has an important application value in the field of vein efficient oxygen supply.

The present application has the following beneficial effects:

(1) The present application provides a microbubble dispersion system stabilized with polydopamine nanoparticles for highly-efficient intravenous oxygen supply and a method for preparing the same, which solves the problems of the traditional microbubble dispersion system stabilized with surfactant molecules that oxygen carrying capacity is low, the system is unstable, and thus it is difficult to realize intravenous oxygen supply.

(2) In the method used in the present application, no harmful substances are generated in the experimental process, and the prepared oxygen microbubbles stabilized with polydopamine nanoparticles have good biocompatibility, are non-toxic and non-irritating to human bodies, and can be applied to the biomedical field.

(3) The interface of the microbubbles prepared by the present application is covered with a relatively compact shell layer of polydopamine nanoparticles, which can well prevent bubbles from fusing, so that the microbubbles can stably carry oxygen for a long time.

(4) The oxygen microbubbles stabilized with polydopamine nanoparticles prepared by the present application can effectively control the rapid release of oxygen wrapped in the oxygen microbubbles in the extremely anoxic solution, thus providing a basis for realizing highly-efficient intravenous oxygen supply.

DESCRIPTION OF EMBODIMENTS

The present application will be described with reference to the following examples, but the present application is not limited to the following examples.

Example 1

Figure 1:
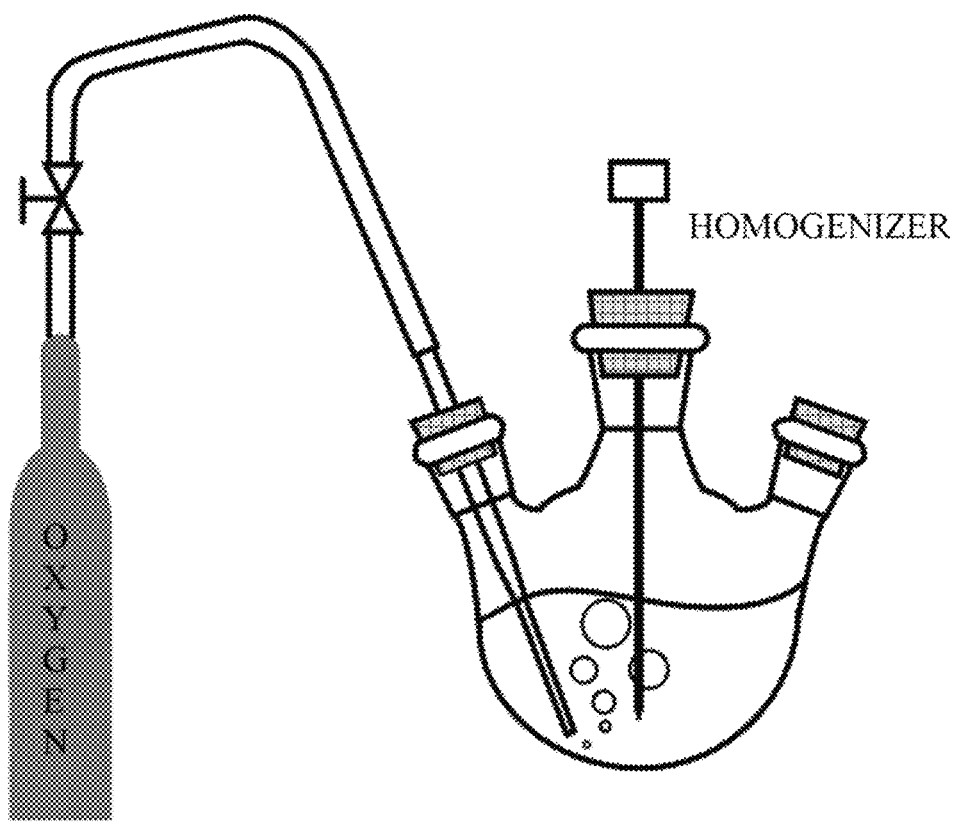
FIG. 1 is a schematic diagram of a device for preparing a microbubble dispersion system stabilized with polydopamine nanoparticles.

Preparation of an Oxygen Microbubble Dispersion System Stabilized with Polydopamine Nanoparticles With reference to the device in FIG. 1, the oxygen microbubble dispersion system stabilized with polydopamine nanoparticles is prepared by the method of the present application, and the specific steps are as follows:

(1) 20 mg of dopamine, 5 mg of polylysine and 120 mg of a chitosan quaternary ammonium salt were dissolved in 10 mL of deionized water, and then 1 mL of a tris salt buffer solution with pH=8.5 was added to adjust the pH value of the mixed solution to make the mixed solution alkaline.

Figure 2:
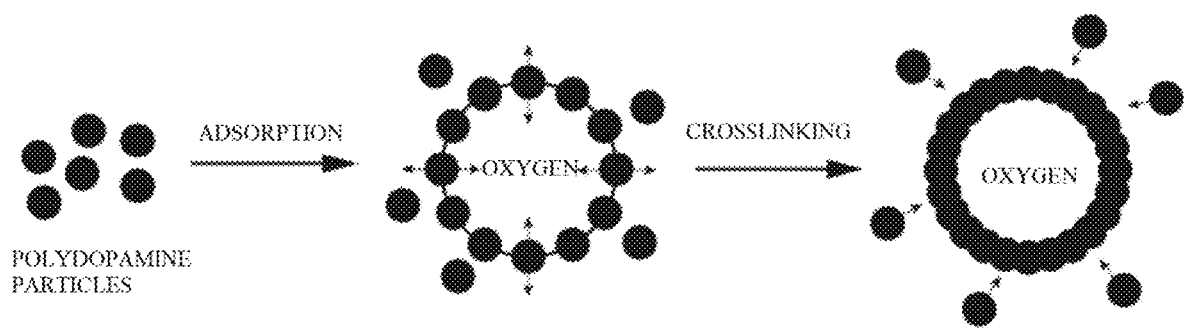
FIG. 2 is a schematic diagram of the adhering and crosslinking solution of polydopamine nanoparticles at the oxygen-water interface in Example 1 of the present application.

(2) Oxygen was introduced into the solution obtained in step (1) at a flow rate of 1 L/min, the rotating speed of a high-speed dispersion homogenizer was adjusted to 12000 rpm, and the oxygen was sheared into microbubbles by the homogenizer. The dopamine was oxidized and self-polymerized under alkaline conditions to form polydopamine nanoparticles, which adhered to the interface of microbubbles to form a compact shell layer of polydopamine particles (as shown in FIG. 2); the high-speed dispersion homogenizer was turned off after homogenizing for 5 min, and introduction of oxygen was continued for 2 min until the solution was brownish black.

Figure 3A:
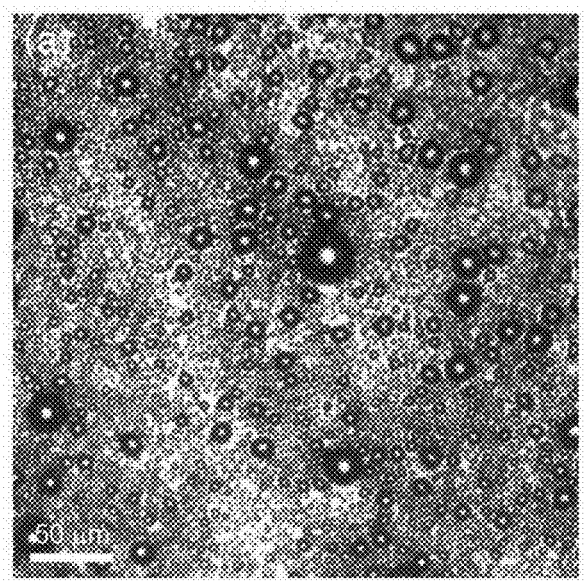
FIG. 3A is an optical image of a microbubble dispersion solution stabilized with polydopamine nanoparticles obtained in step (3) in Example 1 of the present application.

(3) 1 ml of a 4% glutaraldehyde solution was added into the solution obtained in step (2), and the solution was homogenized with the high-speed dispersion homogenizer at 12000 rpm for 3 min, and then stirred at 1000 rpm for 30 min at room temperature to solidify the shell layer of polydopamine particles adhered to the interface of the microbubbles, thus obtaining a microbubble dispersion solution stabilized with polydopamine nanoparticles, as shown in FIG. 3A.

Figure 3B:
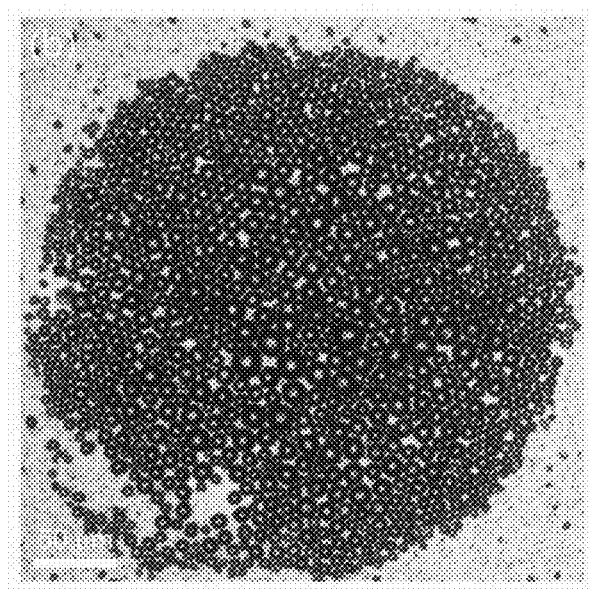
FIG. 3B is an optical image of an oxygen microbubble dispersion stabilized with polydopamine nanoparticles obtained in step (4) in Example 1 of the present application.
Figure 4:
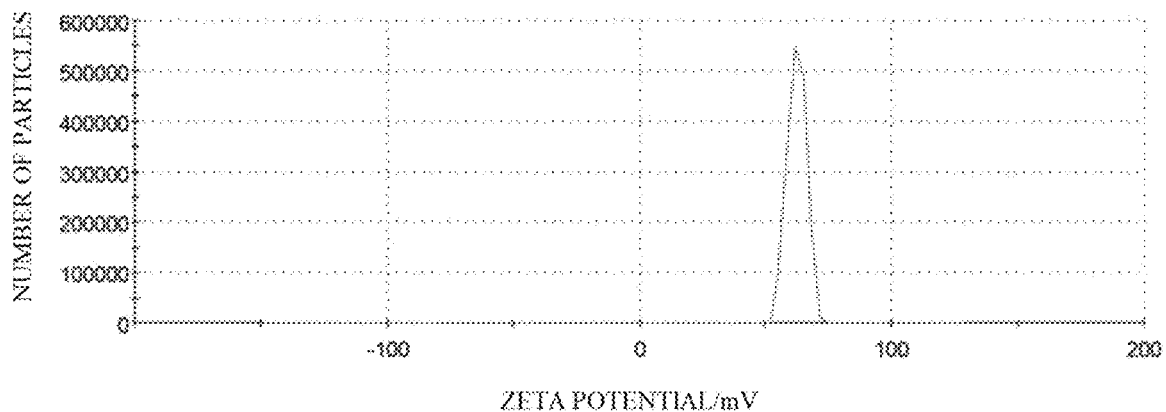
FIG. 4 is the potential measurement of the microbubble dispersion liquid stabilized with polydopamine nanoparticles in Example 1 of the present application.

(4) The microbubble dispersion solution stabilized with polydopamine nanoparticles obtained in step (3) was diluted by deionized water for 5 times, and then the diluted solution was filtered with a filter paper with a pore size of 2.5 μm and a glass funnel to remove redundant polydopamine nanoparticles and other reagents not adsorbed on the interface of the microbubbles, then the microbubbles left on the filter paper were washed with deionized water and filtered again, and finally the microbubbles were flushed into glass bottles for storage with deionized water to obtain an oxygen microbubble dispersion solution stabilized with polydopamine nanoparticles stably dispersed in water, as shown in FIG. 3B. The surface of the microbubbles had a positive charge of +62.5 mV, which proved that there was a polydopamine shell layer on the surface of the microbubbles.

Example 2

Figure 5:
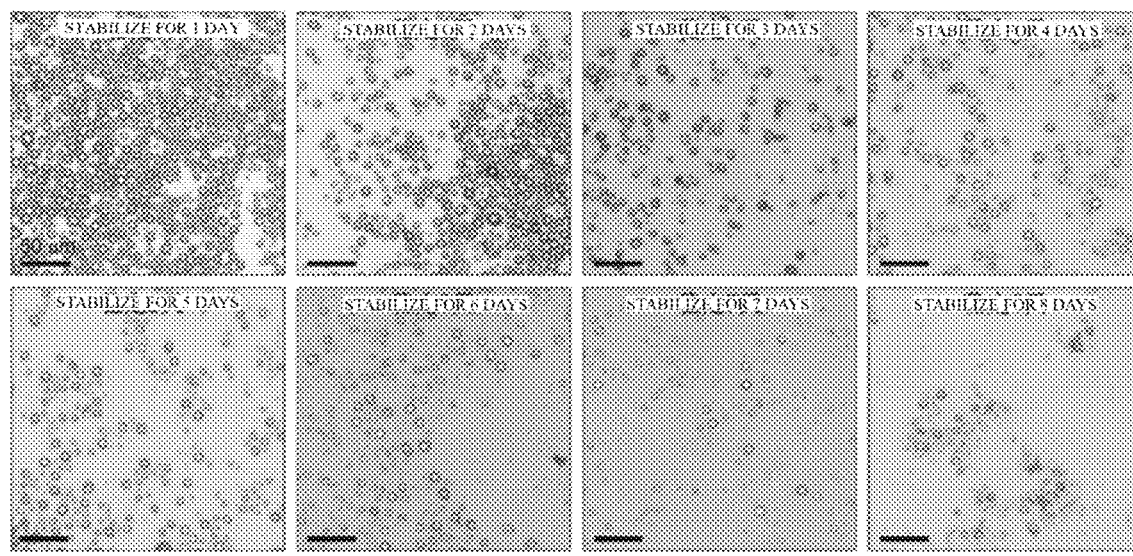
FIG. 5 is an optical image showing the time-varying morphology of the microbubbles stabilized with polydopamine nanoparticles in Example 2 of the present application.
Figure 6A:
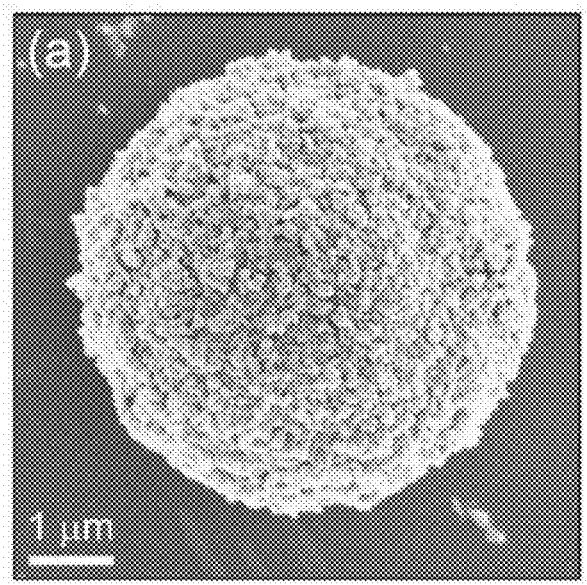
FIG. 6A is a scanning electron microscope image of the microbubbles stabilized with polydopamine nanoparticles in Example 2 of the present application.
Figure 6B:
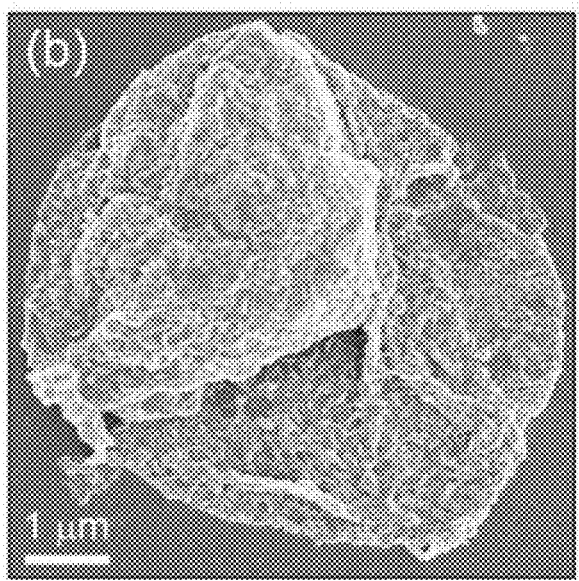
FIG. 6B is a scanning electron microscope image when the microbubbles stabilized with polydopamine nanoparticles collapse in Example 2 of the present application.

Changes of Morphology of the Microbubbles Stabilized with Polydopamine Nanoparticles with Time A dispersion liquid of microbubbles in water stabilized with polydopamine nanoparticles was stored at room temperature. The morphological changes of the microbubbles in water were regularly observed by an optical microscope, as shown in FIG. 5. A scanning electron microscope was used to observe the surface morphology of the microbubbles stabilized with polydopamine particles. As shown in FIG. 6A, there were compact nano-sized polydopamine particles at the interface of microbubbles. After standing and storing for one week, some microbubbles stabilized with polydopamine nanoparticles shrank or even collapsed, resulting in the release of oxygen wrapped in the shell layer of polydopamine nanoparticles, as shown in FIG. 6B.

Example 3

Figure 7:
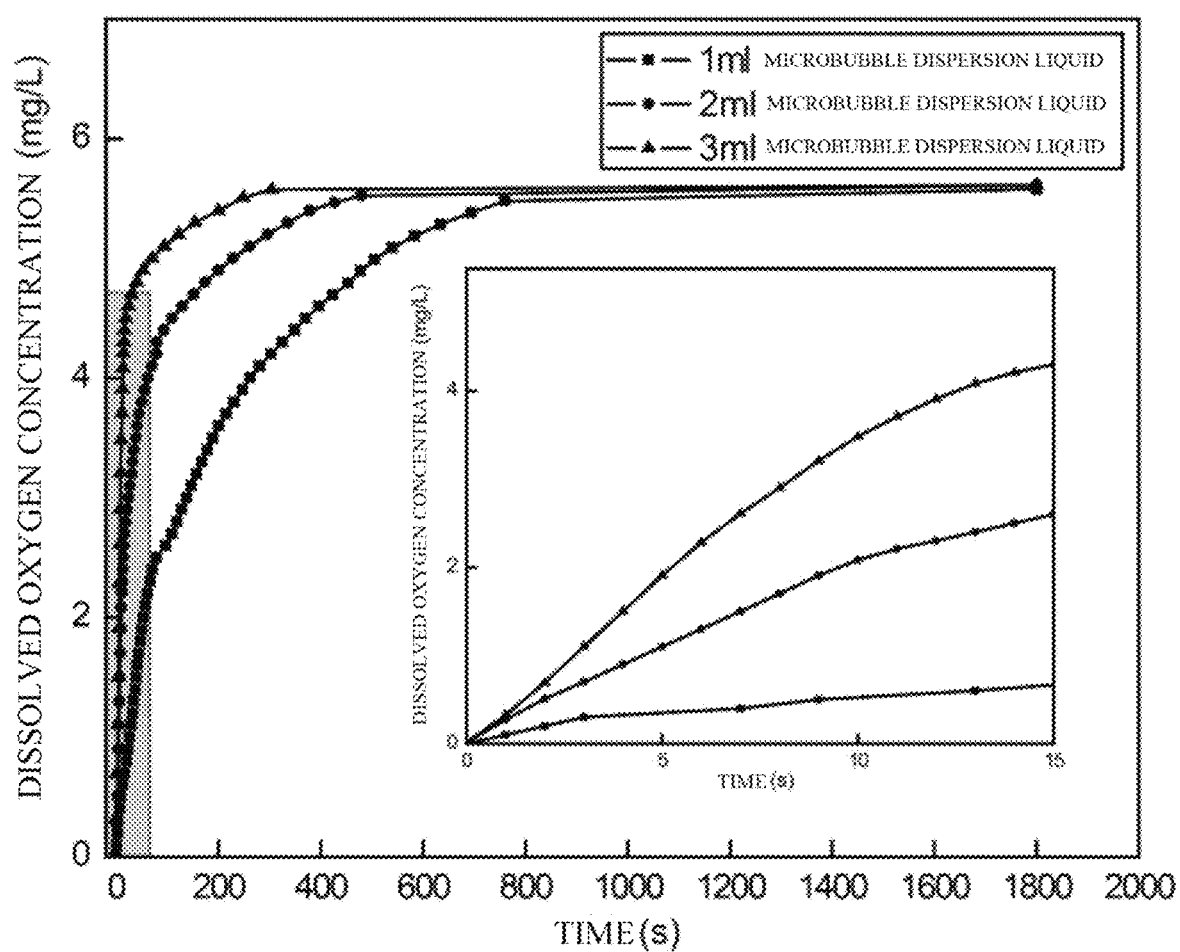
FIG. 7 is a time-intensity curve of the oxygen release from the microbubbles stabilized with polydopamine nanoparticles in Example 3 of the present application in vitro.

Oxygen Release Rate of Oxygen Microbubbles Stabilized with Polydopamine Nanoparticles In Vitro (1) Under the condition of a room temperature of 20° C., the dissolved oxygen concentration of normal saline was reduced to 0 mg/L with pure $N_2$ to prepare an extremely anoxic solution. Six hours after the successful preparation of the oxygen microbubbles stabilized with polydopamine nanoparticles, 1 ml of an oxygen-carrying microbubble dispersion liquid was injected into 10 ml of a sealed extremely anoxic solution, and the changes of the dissolved oxygen in the solution was detected by a dissolved oxygen analyzer; the release of $O_2$ from the oxygen-carrying microbubbles in extremely anoxic saline was continually observed for about 30 min, as shown in FIG. 7. Oxygen microbubbles stabilized with polydopamine nanoparticles could effectively release $O_2$ in the extremely anoxic saline, and 1 ml of the oxygen-carrying microbubble dispersion liquid could increase the dissolved oxygen content of the solution to about 5.5 mg/ml within 800 s, basically recovering to the saturated oxygen content in water.

(2) Under the condition of a room temperature of 20° C., the dissolved oxygen concentration of normal saline was reduced to 0 mg/L with pure $N_2$ to prepare an extremely anoxic solution. Six hours after the successful preparation of the oxygen microbubbles stabilized with polydopamine nanoparticles, 2 ml of an oxygen-carrying microbubble dispersion liquid was injected into 10 ml of a sealed extremely anoxic solution, and the changes of the dissolved oxygen in the solution was detected by a dissolved oxygen analyzer; the release of $O_2$ from the oxygen-carrying microbubbles in extremely anoxic saline was continually observed for about 30 min, as shown in FIG. 7. Oxygen microbubbles stabilized with polydopamine nanoparticles could effectively release $O_2$ in the extremely anoxic saline, and 2 ml of the oxygen-carrying microbubble dispersion liquid could increase the dissolved oxygen content of the solution to about 5.5 mg/ml within 500 s, basically recovering to the saturated oxygen content in water.

(3) Under the condition of a room temperature of 20° C., the dissolved oxygen concentration of normal saline was reduced to 0 mg/L with pure $N_2$ to prepare an extremely anoxic solution. Six hours after the successful preparation of the oxygen microbubbles stabilized with polydopamine nanoparticles, 3 ml of an oxygen-carrying microbubble dispersion liquid was injected into 10 ml of a sealed extremely anoxic solution, and the changes of the dissolved oxygen in the solution was detected by a dissolved oxygen analyzer; the release of $O_2$ from the oxygen-carrying microbubbles in extremely anoxic saline was continually observed for about 30 min, as shown in FIG. 7. Oxygen microbubbles stabilized with polydopamine nanoparticles could effectively release $O_2$ in the extremely anoxic saline, and 3 ml of the oxygen-carrying microbubble dispersion liquid could increase the dissolved oxygen content of the solution to about 5.5 mg/ml within 200 s, basically recovering to the saturated oxygen content in water.

What is claimed is:

1. A method for preparing a microbubble dispersion system stabilized with polydopamine nanoparticles for highly-efficient intravenous oxygen supply, wherein the method comprising the following steps:
   (1) dissolving dopamine, a chitosan quaternary ammonium salt and polylysine in deionized water, and then adding a tris buffer solution to adjust a pH value of mixed solution to make the mixed solution alkaline; wherein a concentration of the dopamine is 10-40 mg/mL, a concentration of the polylysine is 1-40 mg/ml, and a concentration of the chitosan quaternary ammonium salt is 20-400 mg/ml; a mass ratio of the polylysine to the dopamine is 0.25-1; a mass ratio of the chitosan quaternary ammonium salt to the dopamine is 2-10;
   (2) introducing oxygen into the solution obtained in the step (1), shearing the oxygen into microbubbles by using a high-speed dispersion homogenizer, oxidizing and self-polymerizing the dopamine under alkaline conditions to form polydopamine nanoparticles, which adhere to an interface of the microbubbles to form a compact shell layer of polydopamine particles, then turning off the high-speed dispersion homogenizer, and continuously introducing oxygen until the solution is brownish black;
   (3) adding a glutaraldehyde solution into the solution obtained in the step (2), fully mixing by the high-speed dispersion homogenizer, and then stirring to solidify the shell layer of polydopamine particles adhered to the interface of the microbubbles; wherein a volume fraction of the glutaraldehyde solution is 2%-6.5%, and a dosage of the glutaraldehyde solution is 1 ml-5 ml; a rotating speed of the high-speed dispersion homogenizer is 10,000 rpm-14,000 rpm, and a homogenization time is 1-4 min; the stirring is carried out at 20-40° C. for 30 min-2 h; and
   (4) diluting a microbubble dispersion solution stabilized with the polydopamine nanoparticles obtain in the step (3), filtering and washing to remove redundant polydopamine nanoparticles and reagents which are not adhered on the interface of the microbubbles, and finally obtaining an oxygen microbubble dispersion system stabilized with the polydopamine nanoparticles stably dispersed in water.

2. The method for preparing a microbubble dispersion system stabilized with polydopamine nanoparticles according to claim 1, wherein in step (1), the adding a tris buffer solution to adjust a pH value of mixed solution to make the mixed solution alkaline is adding Tris-HCl to the mixed solution to adjust the pH value of the mixed solution to 7.5-9.0.

3. The method for preparing a microbubble dispersion system stabilized with polydopamine nanoparticles according to claim 1, wherein in the step (2), a flow rate of introducing oxygen is 0.5-2 L/min, a rotating speed of the high-speed dispersion homogenizer is 10,000 rpm-14,000 rpm, and a homogenization time is 3-6 min; introduction of oxygen is continued until the solution is brownish black.

4. The method for preparing a microbubble dispersion system stabilized with polydopamine nanoparticles according to claim 1, wherein in the step (4), a pore diameter of a filter paper is 1 μm-11 μm.

5. A microbubble dispersion system stabilized with polydopamine nanoparticles prepared by the method of claim 1.

* * * * *